(12) United States Patent
Mei et al.

(10) Patent No.: US 7,435,838 B2
(45) Date of Patent: Oct. 14, 2008

(54) CRYSTALLINE CITALOPRAM DIOL INTERMEDIATE ALKALI

(75) Inventors: Runan Mei, Hangzhou (CN); Dianwu Guo, Hangzhou (CN); Shulong Wang, Hangzhou (CN)

(73) Assignee: Hangzhou Minsheng Pharmaceutical Co. Ltd., Hangzhou, Zhejiang Province (CN)

( * ) Notice: Subject to any disclaimer, the term of this patent is extended or adjusted under 35 U.S.C. 154(b) by 51 days.

(21) Appl. No.: 10/583,360

(22) PCT Filed: Dec. 6, 2004

(86) PCT No.: PCT/CN2004/001418

§ 371 (c)(1), (2), (4) Date: Jun. 19, 2006

(87) PCT Pub. No.: WO2005/092875

PCT Pub. Date: Oct. 6, 2005

(65) Prior Publication Data

US 2007/0117992 A1    May 24, 2007

(30) Foreign Application Priority Data

Dec. 19, 2003  (CN) .................. 2003 1 0123623
May 26, 2004  (CN) .................. 2004 1 0044335

(51) Int. Cl.
  *C07D 307/78*  (2006.01)
  *C07D 307/87*  (2006.01)
  *C07D 307/93*  (2006.01)

(52) U.S. Cl. .................. 549/476; 549/471; 549/469

(58) Field of Classification Search .................. 549/476, 549/469, 471
See application file for complete search history.

(56) References Cited

U.S. PATENT DOCUMENTS

| 4,136,193 | A | | 1/1979 | Bogeso et al. |
| 4,560,884 | A | | 12/1985 | Whittecar |
| 4,650,884 | A | * | 3/1987 | Bogeso .................. 549/467 |
| 4,943,590 | A | * | 7/1990 | Boegesoe et al. .......... 514/469 |
| 4,945,590 | A | | 8/1990 | Ogura |
| 6,258,842 | B1 | | 7/2001 | Petersen et al. |
| 6,291,689 | B1 | | 9/2001 | Petersen et al. |
| 6,365,747 | B1 | | 4/2002 | Dall'Asta et al. |

FOREIGN PATENT DOCUMENTS

| CN | 1339435 A | | 3/2002 |
| CN | 1339436 A | | 3/2002 |
| CN | 1366525 A | | 8/2002 |
| CN | 1366526 A | | 8/2002 |
| CN | 1404475 A | | 3/2003 |
| CN | 1406236 A | | 3/2003 |
| CN | 1418205 A | | 5/2003 |
| CN | 1423644 A | | 6/2003 |
| CN | 1492861 A | | 4/2004 |
| CN | 1496358 A | | 5/2004 |
| CN | 1510024 A | | 7/2004 |
| DE | 2657271 | | 3/1978 |
| GB | 2356199 | | 5/2001 |
| GB | 2357762 | | 7/2001 |
| WO | WO 98/19511 | | 5/1998 |
| WO | WO 98/19512 | | 5/1998 |
| WO | WO 00/12044 | | 3/2000 |
| WO | WO 03/000672 | | 1/2003 |
| WO | WO03000672 A1 | | 1/2003 |
| WO | WO03051861 A1 | | 6/2003 |
| WO | WO 03/072565 | | 9/2003 |
| WO | WO 2004/056754 | * | 7/2004 |

OTHER PUBLICATIONS

Li et al. STN Accession No. 2005:519249; Document No. 143:59681 Abstract of CN 15110024).*
Experimental Organic Chemistry, James F. Norris, Published 1924, pp. 3 and 4.*
Norris, 1924, Experimental Organic Chemistry, McGraw-Hill Book Company Inc. pp. 3).*
A. Gravem, "A double-blind comparison of citalopram (Lu 10-171) and amitriptyline in depressed patients", Acta Psychiatr. Scand. 1987, vol. 75, p. 478-486.

* cited by examiner

*Primary Examiner*—D. Margaret Seaman
*Assistant Examiner*—Nizal S Chandrakumar
(74) *Attorney, Agent, or Firm*—Jacobson Holman PLLC (57) ABSTRACT

The present invention relates to the diol intermediate of citalopram useful for treatment of depression, which is the crystal of free base of 3-hydroxylmethyl-4-[1-(4-fluorophenyl)-1-hydroxyl-4-(dimethylamino)]butylbenzonitrile and the method of crystallization thereof. The present invention has disclosed the method to prepare pure citalopram and its purified salts through crystallization of the described base; the optical resolution method of citalopram diol intermediate, the method to prepare S-citalopram and its purified salts by crystals mentioned above. The present invention has also disclosed the method to prepare citalopram and its purified salts, S-citalopram and its purified salts, as well as pharmaceutical formulation thereof obtained. Using methods of the present invention, the quality and yield of the product can be significantly improved, and the production cost of the medicinal material can be reduced.

24 Claims, 4 Drawing Sheets

CRYSTALLINE CITALOPRAM DIOL INTERMEDIATE ALKALI

This is a U.S. national stage application of PCT/CN2004/001418 filed Dec. 6, 2004 and published in Chinese.

FIELD OF THE INVENTION

The present invention relates to the diol intermediate of citalopram useful for treatment of depression, more specifically, the pure crystal base of 3-hydroxymethyl-4-[1-(4-fluorophenyl)-1-hydroxyl-4-(dimethylamino)]butylbenzonitrile and the method of purification thereof, and relates to the method of preparing citalopram purified salts from the obtained crystal base. The present invention also relates to the optical resolution method of the described crystal base, the method to prepare S-citalopram purified salts, the method to prepare citalopram and its purified salts, S-citalopram and its purified salts, as well as pharmaceutical formulation obtained thereof.

BACKGROUND OF THE INVENTION

Citalopram is a well-known antidepressant drug. It is a selective, centrally acting serotonin (5-hydroxyltryptamine) reuptake inhibitor, accordingly having antidepressant activities. The antidepressant activity of the compound has been reported in several publications, e.g. J. Hyttel, Prog. Neuro-Psychopharmacol. & Biol. Psychiat.) 1982, 6, 277-295 and A. Gravem, Acta Psychiatr. Scand.) 1987, 75, 478-486. These publications also disclosed the effects of the compound in the treatment of dementia and cerebrovascular disorders. The structure of citalopram is as follows:

II

The synthesis of citalopram was first disclosed in U.S. Pat. No. 4,136,193 in 1977 and in DE2657271 in 1979. They both described the preparation of citalopram. As an antidepressant drug, citalopram has been on market in more than sixty countries. There are many patent publications concerning the preparation of citalopram, for example:

1. The starting material 5-cyanophthalide is subjected to: (1) two successive Grignard reactions with 4-bromofluorophenyl and N,N-dimethylaminopropyl chloride, respectively; (2) hydrolysis of the product in dilute acid to obtain citalopram diol intermediate; (3) ring closure with acid; (4) purification and salt formation with bromic acid to obtain citalopram (U.S. Pat. No. 4,560,884).

2. The starting material 5-aminophthalide is subjected to two successive Grignard reactions, hydrolysis, ring closure by dehydration, diazotization and salt formation with bromic acid to obtain citalopram (WO 98/19512).

3. The starting material 5-cyanophthalide is subjected to Grignard reaction with 4-bromofluorophenyl, hydrolysis, reduction by sodium borohydride, ring closure and a second Grignard reaction with N,N-dimethylaminopropyl chloride to obtain citalopram. (WO 9819511).

4. The starting material 5-cyanophthalide is subjected to Grignard reaction with 4-bromofluorophenyl, hydrolysis, esterification, a second Grignard reaction with N,N-dimethylaminopropyl chloride and hydrolysis with acid to obtain citalopram diol intermediate. The intermediate is then subjected to ring closure with acid, purification, and salt formation with bromic acid to obtain citalopram (WO 0012044).

There are many other methods concerning the preparation of citalopram. No matter which is adopted, many purification processes are required in order to obtain relatively purer product. Though many purification processes which may result in the loss of citalopram are employed, the impurities, especially those having similar structures with the product, are hard to eliminate.

It is well known that some of the impurities are from the early starting materials of citalopram or S-citalopram. For example, depending on different starting materials, 5-cyanophthalide can be converted from 5-bromophthalide, 5-chlorophthalide, 5-aminophthalide, 5-amidophthalide, 5-esterphthalide, 5-methylacylphthalide, 5-oxazolinylphthalide, 5-thiazolinylphthalide, 5-carboxylphthalide or phthalide whose 5-substituted group is $-O-SO_2-(CF_2)_n-CF_3$. Due to the incomplete conversion of the early starting materials, those materials as well as the impurities which resulted from the conversion process have similar structures with 5-cyanophthalide, and will more or less exist among 5-cyanophthalide. They will be further converted into other impurities, which have similar structures with citalopram diol intermediate, in the following process of preparing citalopram diol intermediate. The impurities exist among the early starting materials and the intermediates and have similar structures with those materials or intermediates in different stages. They will be further converted into the impurities which have similar structures with the ultimate product during the synthesis process of citalopram or S-citalopram. One or several previously mentioned impurities, other impurities resulted from the conversion and disposal processes may exist among the citalopram diol intermediate. For instance, there may exit impurities like the following III and/or IV.

III

IV

In Formula III, Z is halogen; $-O-SO_2-(CF_2)_n-CF_3$, wherein n is 0-8; $-CHO$; $-NHR^1$; $-COOR^2$;

—CONR²R³; wherein R² and R³ is hydrogen, alkyl, any substitutional aryl or arylalkyl, R¹ is hydrogen or alkylcarbonyl.

Although there are several disclosed methods such as those in GB2356199, WO03/072565 for purifying citalopram crude product, which can effectively eliminate one or several of the impurities. In GB2356199, a short vacuum distillation is employed, which requires expensive equipments and complex operations. In WO03/072565, complex operations like several salt formation processes and several careful pH adjustments are required. These long purifying processes result in loss of the product while achieving limited results.

It is well-known that citalopram has two enantiomers: S-citalopram and R-citalopram. It is S-citalopram that has the antidepressant activities; R-citalopram hardly has such activities. Presently, S-citalopram salt has been on market. When preparing for S-citalopram, usually chiral organic acid is reacted with the amino group of citalopram diol intermediate. Then the enantiomers are resoluted according to their solubility, or reacted with the 3-substituted hydroxylmethyl of citalopram diol intermediate free base to form diastereomeric esters and then resoluted through crystallization or column chromatography. Among those resolution methods, the most extensively used one is that citalopram diol intermediate is subjected to salt formation with a chiral organic acid and then the obtained enantiomers are resoluted through crystallization. The method is convenient but requires a large amount of chiral organic acid. In addition, WO 03/000672 disclosed a method of resolution non-racemic mixture of S-citalopram and R-citalopram through deposit crystallization. Through separating the deposit and the mother liquor, the enantiomer with a relatively high content was collected in the mother liquor and resoluted. The obtained R-citalopram cannot be used at present. During the stage of resoluting citalopram diol intermediate, the obtained R-citalopram diol intermediate can be effectively used. For instance, WO 03/000672 disclosed a method of converting it into the mixture of R-citalopram and S-citalopram. The mixture was further separated to obtain the racemates of citalopram diol intermediate or mixture of near racemates. It can also be used to form salt with a chiral organic acid and then resoluted or used to prepare citalopram through ring closure.

In GB2357762, citalopram base was purified through crystallization of racemic citalopram free base. The purification of S-citalopram was not yet mentioned, nor was the crystallization of S-citalopram base.

Therefore, a more effective and economical purification method is needed for the industrial production of citalopram. For the preparation of S-citalopram in particular, a more effective and simpler method is needed.

SUMMARY OF THE INVENTION

It has been discovered that quite pure citalopram diol intermediate free base can be obtained. Surprisingly, it has been discovered that the described base can be effectively purified through crystallization. The method is easy to implement and high yield can be achieved. In addition, it has been discovered that using the described base as starting material, pure citalopram or S-citalopram can be effectively prepared. The present invention provides an effective and simple method for purifying citalopram diol intermediate, through the crystallization of the described base, quite pure citalopram diol intermediate can be obtained. Using the purified citalopram diol intermediate as starting material, quite pure citalopram and its acid addition salts can be prepared effectively and simply.

More importantly, it has been discovered that the pure citalopram diol intermediate obtained through crystallization of the described base is able to be resoluted to prepare pure S-citalopram diol intermediate effectively and simply. The obtained S-citalopram diol intermediate is further converted into S-citalopram and its acid addition salts effectively and simply. The present invention provides a novel method for the commercial production of pure S-citalopram, reducing the cockamamie and expensive purification processes.

In another aspect, the present invention also provides a method of resolution the mixture of S-citalopram and R-citalopram that is not entirely racemic. Through the direct crystallization of the crystal base, the mixture is effectively resoluted in the form of free base. The method can be alternated or combined with the resolution method which uses a chiral organic acid as resolving agent, saving the required amount of resolving agent and improving the yield.

Citalopram diol intermediate oil substance and citalopram diol intermediate raw mixture or raw salt can be prepared according to the method described in U.S. Pat. No. 4,560,884: the starting material 5-cyanophthalide is subjected to two successive Grignard reactions with 4-fluorophenyl magnesium halide (e.g. 4-fluorophenyl magnesium bromide) and N,N-dimethylaminopropyl magnesium halide (e.g. N,N-dimethylaminopropyl magnesium chloride); or prepared according to the method described in WO 0012044: the starting material 5-cyanophthalide is subjected to Grignard reaction with 4-fluorophenyl magnesium halide (eg. 4-bromofluorophenyl), hydrolysis, esterification, a second Grignard reaction with N,N-dimethylaminopropyl magnesium halide (e.g. N,N-dimethylaminopropyl magnesium chloride), wherein, the chemical nomination for 5-cyanophthalide is 5-cyano-2-benz[c]furanone, which can be converted from 5-bromophthalide, 5-chlorophthalide, 5-aminophthalide, 5-amidophthalide, 5-esterphthalide, 5-methylacylphthalide, 5-oxazolinylphthalide, 5-thiazolinylphthalide, 5-carboxylphthalide or phthalide whose 5-substituted group is —O—SO₂—(CF₂)ₙ—CF₃. They can also be bought from companies like H•. Lundbeck, a Danish company which sells the commercial product of citalopram diol intermediate mixture.

It has been discovered that citalopram diol intermediate free base, which is, the crystal base of 3-hydroxylmethyl-4-[1-(4-fluorophenyl)-1-hydroxyl-4-(dimethylamino)]butyl-benzonitrile, is a tintless or white crystal with the following chemical structure:

(mixture of S and R)

It has also been discovered a method of preparing crystal product of citalopram diol intermediate and its salt. Through this method, the product obtained is pure and with a good crystal form and the yield is high. Citalopram diol intermediate free base is freed and precipitated in the form of crystal. The free base is subjected to crystallization one or more times to obtain the crystal, the crystal is further subjected to ring closure by dehydration to obtain citalopram. The obtained citalopram is further converted into citalopram salt. The obtained salt is subjected to crystallization one or more times to give citalopram salt. The preferred citalopram salt is hydrobromic salt or hydrochloric salt.

The present invention relates to a method of preparing S-citalopram and its salts. Citalopram diol intermediate base is freed and precipitated in the form of crystal. Purified citalopram diol intermediate base is obtained through crystallization one or more times and then subjected to resolution and ring closure by dehydration to obtain S-citalopram. The obtained S-citalopram is further converted into S-citalopram salts, the obtained salts are subjected to crystallization one or more times to obtain S-citalopram salts.

The citalopram diol intermediate base and its salt prepared through the method provided by the present invention is suitable for resolution. Before resolution, the preferred chemical purity of citalopram diol intermediate base is over 99.8%, while after resolution, the purity of the enantiomer is over 99.9%.

The present invention relates to a method of preparing citalopram, S-citalopram and its salts, which is characterized by: through crystallization of the described base, citalopram diol intermediate free base was purified. Through crystallization, citalopram diol intermediate was freed from its crude salt or crude mixture so that one or more impurities with the following III and/or IV structures was eliminated, so citalopram diol intermediate free base with a chemical purity of over 99.8% (w/w) was easily obtained.

In Formula III, Z is halogen; —O—SO$_2$—(CF$_2$)$_n$—CF$_3$, wherein n is 0-8; —CHO; —NHR$^1$; —COOR$^2$; —CONR$^2$R$^3$; wherein R$^2$ and R$^3$ is hydrogen, alkyl, any substitutional aryl or arylalkyl, R$^1$ is hydrogen or alkylcarbonyl. Pure citalopram or S-citalopram and its salts can effectively be prepared from the obtained pure citalopram diol intermediate.

The present invention overcomes the limitations of the existing technologies, putting forward a novel method of preparing high pure citalopram diol intermediate free base crystal through crystallization. Through ring closure by dehydration of the crystal base, quite pure citalopram is obtained. The obtained citalopram is then subjected to ordinary purifying processes, such as salt formation with hydrobromic acid; the obtained salt is then crystallized and recrystallized to obtain pure citalopram and its salts. Alternatively, the obtained pure citalopram diol intermediate free base crystal can be resoluted to produce pure enantiomer. Through appropriate ring closure of the enantiomer, pure S-citalopram is obtained. Then salt is produced from the obtained base, through the ordinary purifying processes of the salt, such as crystallization or recrystallization, pure citalopram or S-citalopram and its salts can be obtained effectively.

In another aspect, it has been discovered that citalopram diol intermediate free base can be resoluted through crystallization. Through the crystallization of the racemic citalopram diol intermediate free base crystal, a mixture of S- and R-citalopram diol intermediate with more than 50% of one of the enantiomers is resoluted. The obtained pure S-enantiomer is further subjected to ring closure to obtain pure S-citalopram. (Formula II$^1$)

(S- citalopram)

The present invention relates to a method of preparing R-citalopram free base or S-citalopram free base and its acid addition salts. Through the crystallization of the described base, a mixture of S- and R-citalopram diol intermediate with more than 50% of one of the enantiomers is resoluted. The method includes the following steps;

1) Citalopram diol intermediate is precipitated or crystallized from the solution or the solventless oil substance in the form of free base;
2) The precipitate or crystal is separated from the mother liquor or the oil substance;

The remained citalopram diol intermediate optical enantiomers in the mother liquor or the oil citalopram diol intermediate optical enantiomers are resoluted and their optical rotation are improved. Then S- or R-citalopram diol intermediate is separated from the mother liquor. Alternatively, the obtained solventless oil base is converted into S- or R-citalopram through ring closure, S- or R-citalopram is further converted into its acid addition salts. Wherein, S-citalopram diol intermediate is converted into S-citalopram through proper ring closure reaction, R-citalopram diol intermediate is converted into the mixture of S-citalopram and R-citalopram through proper ring closure reaction.

The described proper ring closure reaction by dehydration for conversing S-citalopram diol intermediate into S-citalopram can be the method disclosed in U.S. Pat. No. 4,945,590: S-citalopram diol intermediate (Formula I) is subjected to ring closure via a labile ester in the presence of a base. The described proper ring closure reaction by dehydration for conversing R-citalopram diol intermediate into S-citalopram or the mixture of S-citalopram and R-citalopram can be the method disclosed in U.S. Pat. No. 4,136,193 or WO 03/000672 where sulfuric acid or phosphoric acid with a certain concentration is used as dehydrating agent. The described proper ring closure reaction by dehydration for converting citalopram diol intermediate into citalopram can also be the method disclosed in U.S. Pat. No. 4,136,193 where sulfuric acid or phosphoric acid with a certain concentration is used as dehydrating agent. These are the commonly used proper methods in the preparation of citalopram in this particular domain.

More specifically, the method provided by the present invention of preparing R-citalopram free base or S-citalopram free base and its acid addition salts includes the following steps:

1) The citalopram diol intermediate among the mixture of S- and R-citalopram diol intermediate is precipitated from the solution or directly crystallized from the oil mixture in the form of free base;

2) The precipitate or crystal is separated from the mother liquor or the oil, and then 3) After separation, the mother liquor or the oil is further subjected to precipitation or crystallization. The S- and R-citalopram diol intermediate separated from the mother liquor or the oil is further subjected to ring closure to obtain S- and R-citalopram, or the mixture of S- and R-citalopram. The S-citalopram diol intermediate is subjected to ring closure to obtain S-citalopram, and S-citalopram can further be converted into its corresponding acid addition salts.

In yet another aspect, the present invention relates a method of preparing R-citalopram free base or S-citalopram free base and its acid addition salts. Through the resolution of a mixture of S- and R-citalopram diol intermediate with more than 50% of one of the enantiomers, racemic citalopram diol intermediate salt and R- or S-citalopram diol intermediate salt are obtained. The method includes the following steps:

1) Citalopram diol intermediate is precipitated or crystallized from the solution in the form of salt;

2) The precipitate or crystal is separated from the solution;

3) The remained citalopram diol intermediate salt optical enantiomers in the mother liquor are purified through resolution, and their optical rotation are improved. Then S- or R-citalopram diol intermediate is separated from the mother liquor and converted into S- or R-citalopram through ring closure, and finally converted into its corresponding acid addition salts. Wherein, S-citalopram diol intermediate is converted into S-citalopram through proper ring closure reaction, R-citalopram diol intermediate is converted into the mixture of S-citalopram and R-citalopram through proper ring closure reaction.

Specifically, the method provided by the present invention of preparing R-citalopram free base or S-citalopram free base and its acid addition salts is characterized by:

1) The citalopram diol intermediate among the mixture of S- and R-citalopram diol intermediate salt mixture is precipitated or crystallized from the solution in the form of salt;

2) The precipitate or crystal is separated from the mother liquor, and then

3) After separation, the mother liquor is further subjected to precipitation or crystallization. Then S- and R-citalopram diol intermediate salt is separated from the mother liquor and set free as base. The base is further subjected to ring closure to obtain S- and R-citalopram, or the mixture of S- and R-citalopram. The S-citalopram diol intermediate is subjected to ring closure to obtain S-citalopram, and S-citalopram can further be converted into its corresponding acid addition salts.

In the present invention, through the crystallization of the described base, a mixture of S- and R-citalopram diol intermediate with more than 50% of one of the enantiomers is directly resoluted. The present resolution method can be used in combination with the method disclosed in U.S. Pat. No. 4,943,590, so the resolving agent can be saved and resolution rate can be improved.

Resolution can be carried out by dissolving the racemic citalopram diol intermediate in proper solvent.

In addition, it has been discovered that through the crystallization of the described base, S-citalopram diol intermediate mixture which contains a small amount of R-citalopram diol intermediate or R-citalopram diol intermediate mixture which contains a small amount of S-citalopram diol intermediate can be purified. The optical purity of the purified product is over 95%. The preferred purity is over 98.5%. The more preferred purity is over 99.0%.

Specifically, through the crystallization of the described base, S-citalopram diol intermediate mixture which contains a small amount of R-citalopram diol intermediate or R-citalopram diol intermediate mixture which contains a small amount of S-citalopram diol intermediate can be purified. If citalopram diol intermediate which needs to be purified is in the form of salt, it is first set free as base and then dissolved in the solvent. Then crystallization is carried out by adding citalopram diol intermediate crystal as crystal seed and the precipitate is separated from the mother liquor. Thus the optical purity of citalopram diol intermediate enantiomer is improved. The purified enantiomer base is obtained after the solvent is evaporated, wherein, the ratio of S- and R-enantiomer in the precipitate is between 0.5 and 1.5, the preferred ratio is between 0.8 and 1.2, the most preferred ratio is 1.0, namely racemic crystal base.

In another aspect, the present invention provides a method of preparing citalopram or S-citalopram drug preparations through crystallization of the described base, wherein, the preferred citalopram salt is hydro bromide salt, the preferred S-citalopram salt is oxalate salt. The preferred described preparations are for oral use.

The crystallization of the described base is effective in purifying citalopram diol intermediate free base. In one preferred implementation project of the present invention, citalopram diol intermediate free base prepared according to the method described in U.S. Pat. No. 4,136,193 was directly dissolved in the solvent, and citalopram diol intermediate free base crystal with a purity of over 99.9% (w/w) was obtained. The obtained crystal was dissolved in inert organic solvent and subjected to ring closure in the presence of ordinary dehydrating agent such as sulfuric acid or phosphoric acid with a certain concentration to obtain pure citalopram free base. And through salt formation and recrystallization of the obtained free base, citalopram salt with a purity of over 99.9% (w/w) was obtained.

In another preferred implementation project of the present invention, the hydrochloric acid salt of citalopram diol intermediate, which had a highest purity of 94.6% (w/w) and contained 3% (w/w) of the previously described impurity of Formula III (wherein, Z is Br), was disposed with activated carbon and recrystallized once. After that, the impurity constituted 2.9% (w/w) (wherein, Z is Br). Then after crystallization, the obtained crystal was suspended in isopropyl ether and disposed with NaOH solution; the organic phase was dried under vacuum and part of the isopropyl ether was recovered; the residue, in which there still remained some isopropyl ether, was crystallized by adding n-heptane into it. The obtained crystal was recrystallized in 70% ethanol solution and citalopram diol intermediate free base crystal with a purity of over 99.9% (w/w) was obtained. The intermediate was dissolved in inert organic solvent and subjected to ring closure in the presence of 85% $H_3PO_4$ as dehydrating agent to obtain citalopram free base. Through salt formation and recrystallization of the obtained citalopram free base, citalopram salt with a purity of over 99.9% (w/w) was obtained.

Preparing citalopram through the present invention, not only the quality of the product is improved simply and effectively, but also the yield of is improved significantly, and the production cost of the medicinal material is also reduced.

Figure 2:
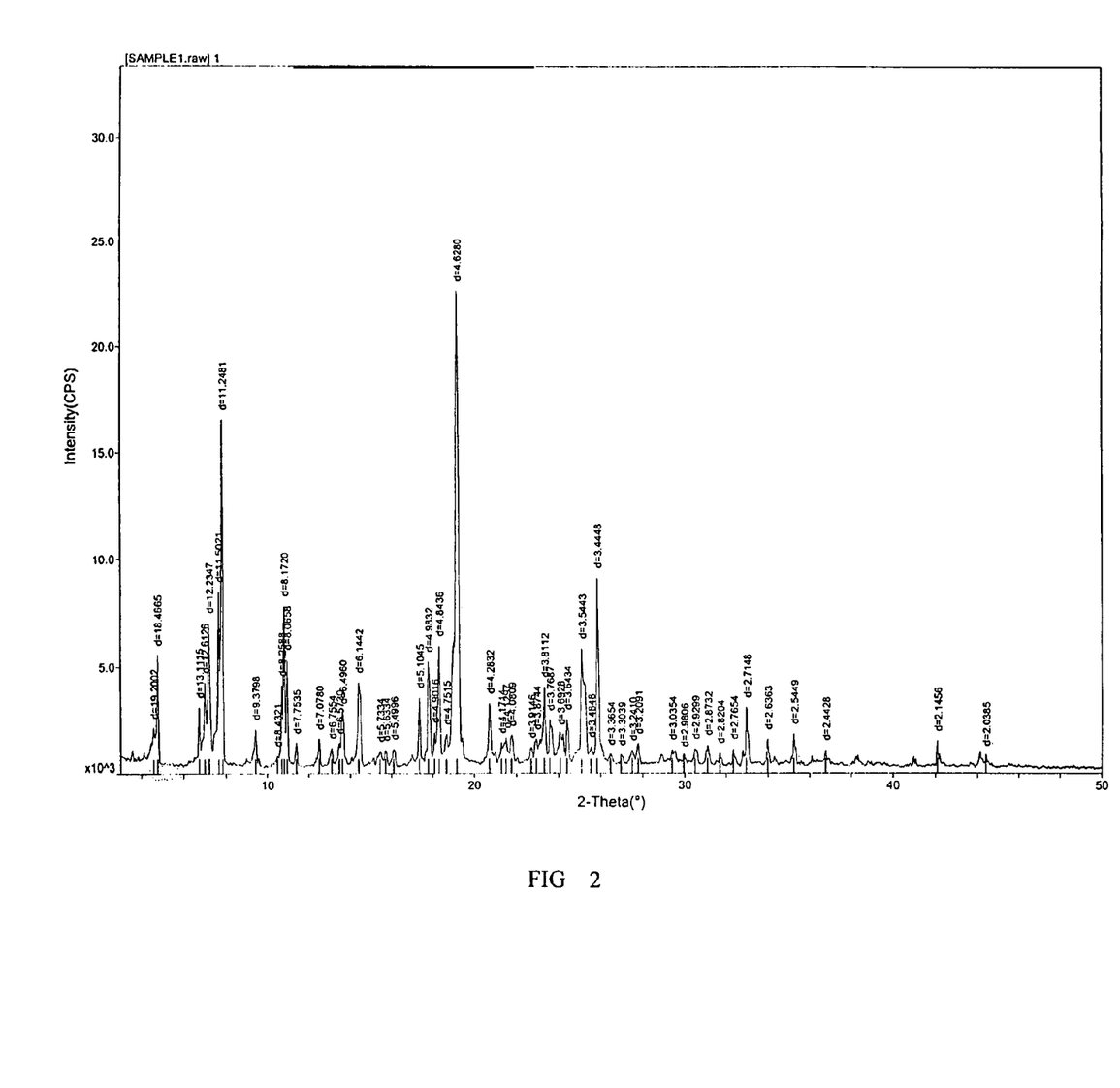
FIG. 2: The XRD spectra of the prepared citalopram diol intermediate base crystal of FIG. 1.
Figure 4:
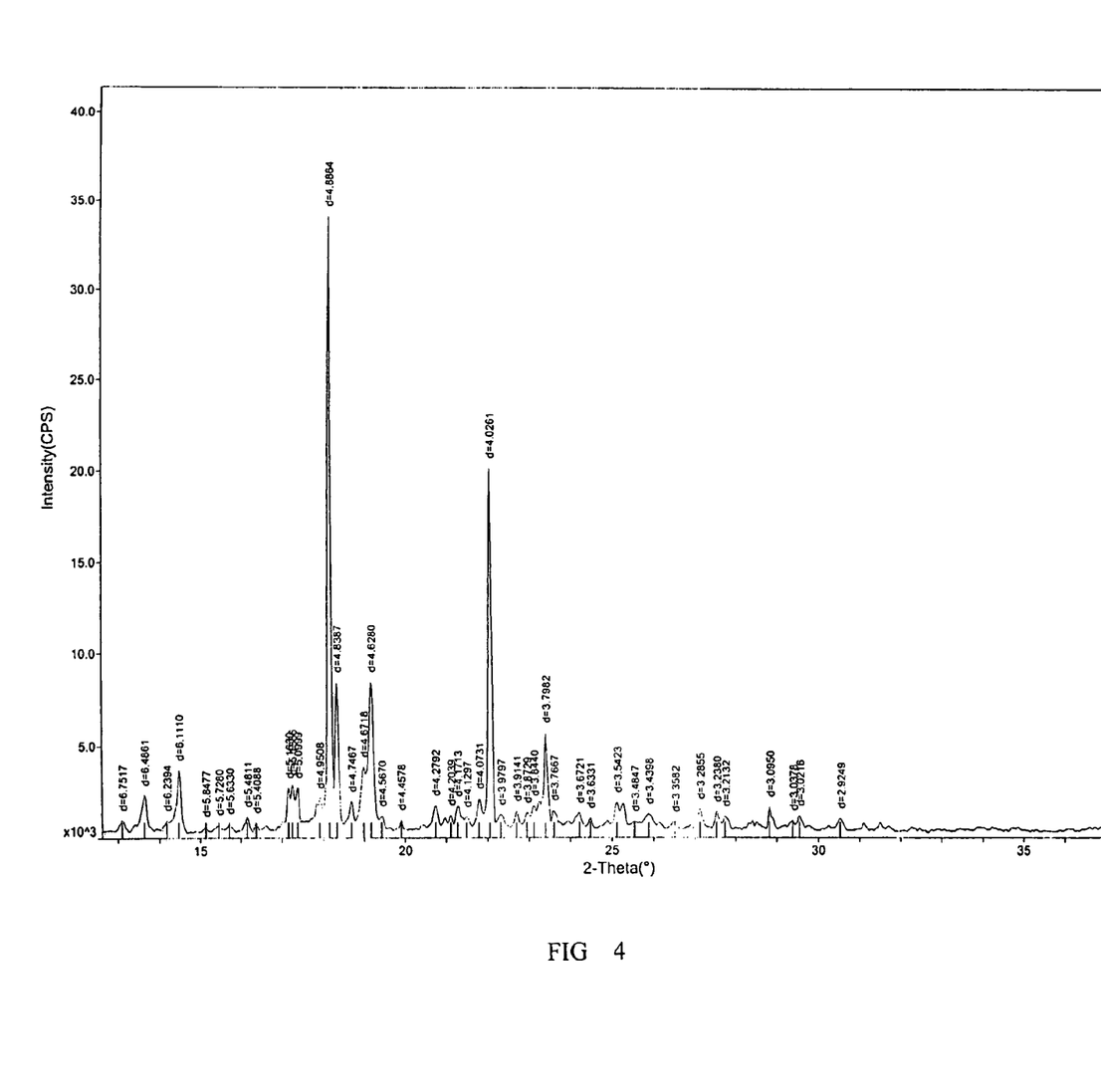
FIG. 4: The XRD spectra of the prepared citalopram diol intermediate base crystal of FIG. 3.

The purity of citalopram diol intermediate free base is over 99.8% (w/w), and the still preferred purity is over 99.9% (w/w). According to the present invention, citalopram diol intermediate free base is found to be a stable white or tint less, aciform and shining crystal. It is discovered that citalopram diol intermediate free base has more than one crystal form. For example, the crystal crystallized from the mixed solvent of isopropyl ether and n-heptane (v/v=1:2) has a extrapolate starting temperature of the DSC measured melting point (DSC, Onset) of 98.63° C., the peak value (DSC, Onset) of 104.18° C. and the enthalpy ($\Delta H$) of 88.13 J/g; for the XRD spectra of which, refer to FIG. 2. The crystal crystallized from 70% ethanol solution has a extrapolate starting temperature of the DSC measured melting point (DSC, Onset) of 51.69° C., the peak value (DSC, Onset) of 59.28° C. and the enthalpy ($\Delta H$) of 38.27 J/g, for the XRD spectra of which, refer to FIG. 4.

The term "crude salt" and "crude mixture" refers to the salt and the mixture that contains the impurities of Formula of III and IV, the intermediates and other impurities resulted from the conversion and disposal processes, respectively.

The described crude salt can be separated from the reaction mixture and primarily purified, such as by recrystallization once, and/or disposed with active carbon or silica gel. The rude reaction mixture can primarily be purified, such as by active carbon or silica gel in the presence of acid, and the formed salt is then disposed by the methods which are already known in this domain. The described salt can be separated in the form of precipitate or kept in solvent such as water and ethanol solution.

Similarly, the crude mixture of citalopram diol intermediate can be synthesized from the described compounds according to any of the previously described methods, or primarily purified, such as by active carbon or silica gel.

Citalopram diol intermediate base can be freed from its crude salt by dissolving the crude salt in the mixture of water and organic solvent and then adding base to the mixture. The described organic solvent can be toluene, isopropyl ether or any other proper solvent; the described base can be any proper base, while NaOH or $NH_3$ is preferred. Similarly, citalopram diol intermediate base can be freed from its crude mixture through disposal with base when needed.

Before the described base is precipitated in the form of crystal, the crude salt of citalopram diol intermediate can further be purified and extracted. It can be separated as follows: the organic phase is separated and the solvent is evaporated so that the described base is obtained (the most likely form of which is oil substance), then the described base is crystallized from proper solvent. The crystallized citalopram diol intermediate free base can be recrystallized in either the same or different solvent.

The solvent used for the crystallization of citalopram diol intermediate can be the proper single component or non-single component solvent that can dissolve citalopram diol intermediate free base. For example: alcohol such as methanol, ethanol; hydrocarbon such as hexane, heptane, cyclohexane; ether such as THF, ethyl ether, isopropyl ether; aromatic hydrocarbon; acetonitrile; acetone; ethyl acetate etc.; or the proper mixture of them. The solvent can also be the bicomponent or multicomponent mixture of water and some water-soluble solvents such as methanol, ethanol, propanol and acetone of a proper proportion. Wherein, the preferred are $C_{1-4}$ alcohol, the bicomponent or multicomponent mixture of $C_{1-4}$ alcohol and water, C>4 ester, $C_{3-8}$ hydrocarbon and/or cycloparaffin, the mixture of C>3 ester and/or cycloparaffin; the more preferred are 60%~90% methanol solution, 60%~90% ethanol solution, isopropyl ether, the mixture of isopropyl ether and hexane or heptane; the most preferred are 70% ethanol solution, the mixture of isopropyl ether and hexane (v/v=1:2), the mixture of isopropyl ether and heptane (V/V=1:2). The other proper solvents can easily be decided by a person of ordinary skill in the art. The crystallization can be carried out either by evaporating the solvent or by cooling down the solution. The crystallization temperature is different according to the solvent and the crystallization mode, which can easily be decided by ordinary technicians of the present domain. The crystallization temperature can be any proper temperature between −40° C. and the boiling point of the solvent, the preferred temperature is between −20° C. and 60° C., the more preferred temperature is between −5° C. and room temperature. Citalopram diol intermediate can also be crystallized directly from the oil substance without adding any solvent. The conditions of crystallization can easily be decided by ordinary technicians of the present domain.

Citalopram diol intermediate free base can be resoluted through crystallization. Through the crystallization of the racemic citalopram diol intermediate free base crystal, a mixture of S- and R-citalopram diol intermediate with more than 50% of one of the enantiomers is resoluted. The resolution can be carried out by dissolving the racemic citalopram diol intermediate in proper solvent. The solvent used is the same as that described previously, it can be methanol, ethanol, acetone, acetonitrile, ethyl ether, toluene etc. and the mixture of them: methanol and water, ethanol and water, acetone and water, acetonitrile and water etc. The resolution can also be carried out directly in the oil substance without adding any solvent.

Through ordinary purification, the purity of citalopram free base or S-citalopram free base and their acid addition salts obtained after ring closure through the present invention is over 99.5% (w/w), the preferred purity is 99.8% (w/w), and the purity of S-citalopram free base and its acid addition salts is over 97% (w/w), the preferred purity is 99% (w/w). Wherein, ordinary purification refers to: the product is disposed with active carbon and/or silica gel; the free base is purified through salt formation with acid, and/or the salt is extracted and set free with base, and/or the salt is purified through crystallization.

The racemate used for resolution can either be the obtained purified or unpurified citalopram diol intermediate oil substance or its hydrobromic salt, sulfuric salt, hydrochloric salt and oxalate salt etc., preferably the quite pure citalopram diol intermediate free base prepared through the present invention.

EXAMPLES

Example 1

Preparation of High Pure Citalopram Diol Intermediate Base Crystal Racemate

Figure 1:
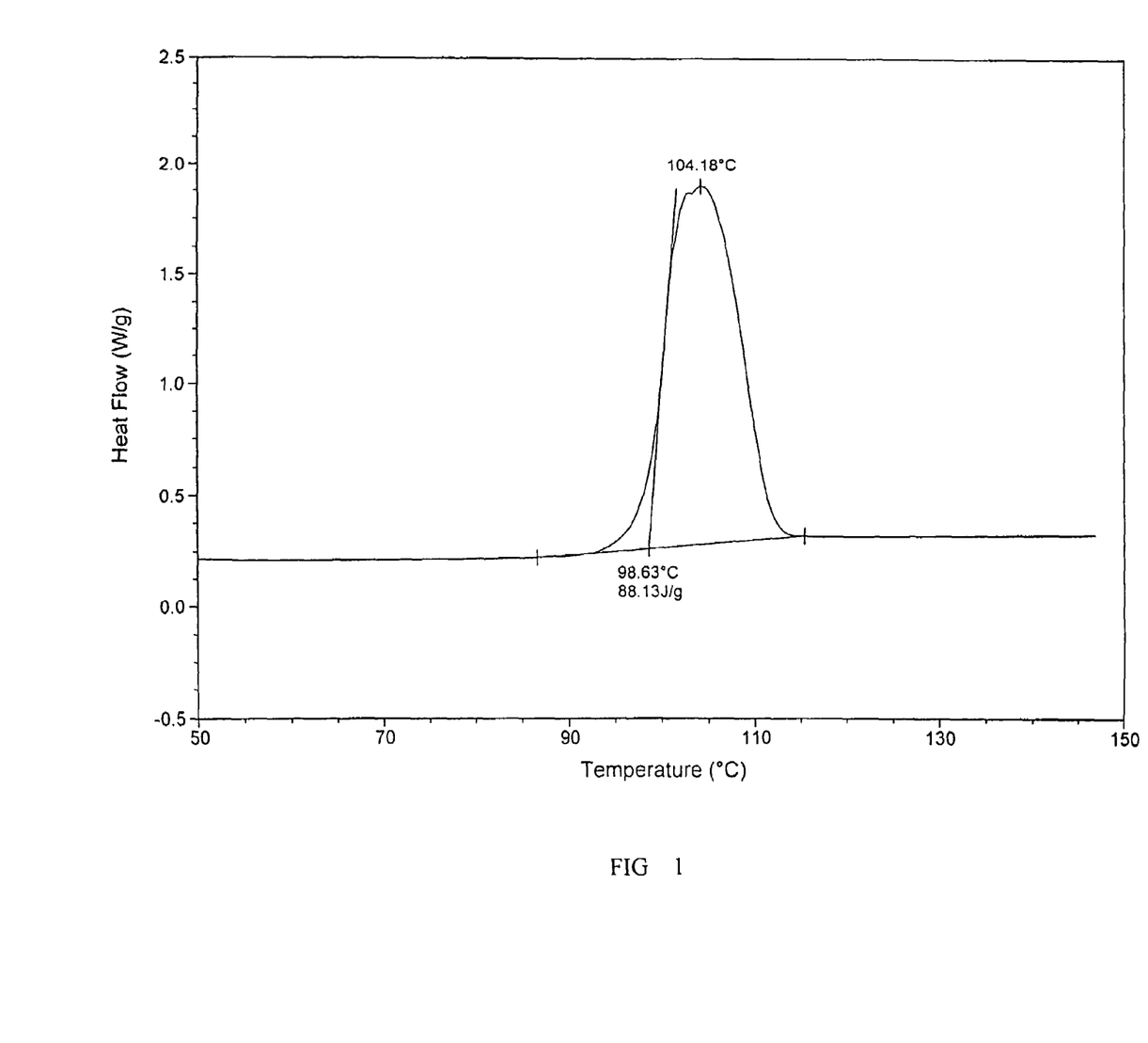
FIG. 1: The DSC profile of citalopram diol intermediate base crystal prepared as described in Example 1, where isopropyl ether was used as solvents.

A. To 100 g citalopram diol intermediate free base oil substance, 200 mL isopropyl ether was added and the mixture was heated until the oil substance was dissolved entirely. Then 400 ml n-heptane was added during mixing and the solution was stirred and placed aside at 5° C. After about 24 hours, a large amount of crystal was crystallized. The solution was filtrated and high pure racemic citalopram diol intermediate base crystal was obtained. After dried, its melting point was measured with thermometer, which is 96-98° C. Its extrapolate starting temperature of the DSC measured melting point (DSC, Onset) is 98.63° C., the peak value (DSC, Onset) is 104.18° C., (refer to FIG. 1), the enthalpy is 88.13 J/g. For the XRD Spectra, refer to FIG. 2. The purity of the product was 99.9% (HPLC, area normalization method), and 95.2 g product was obtained (the yield was 95.2%).

Figure 3:
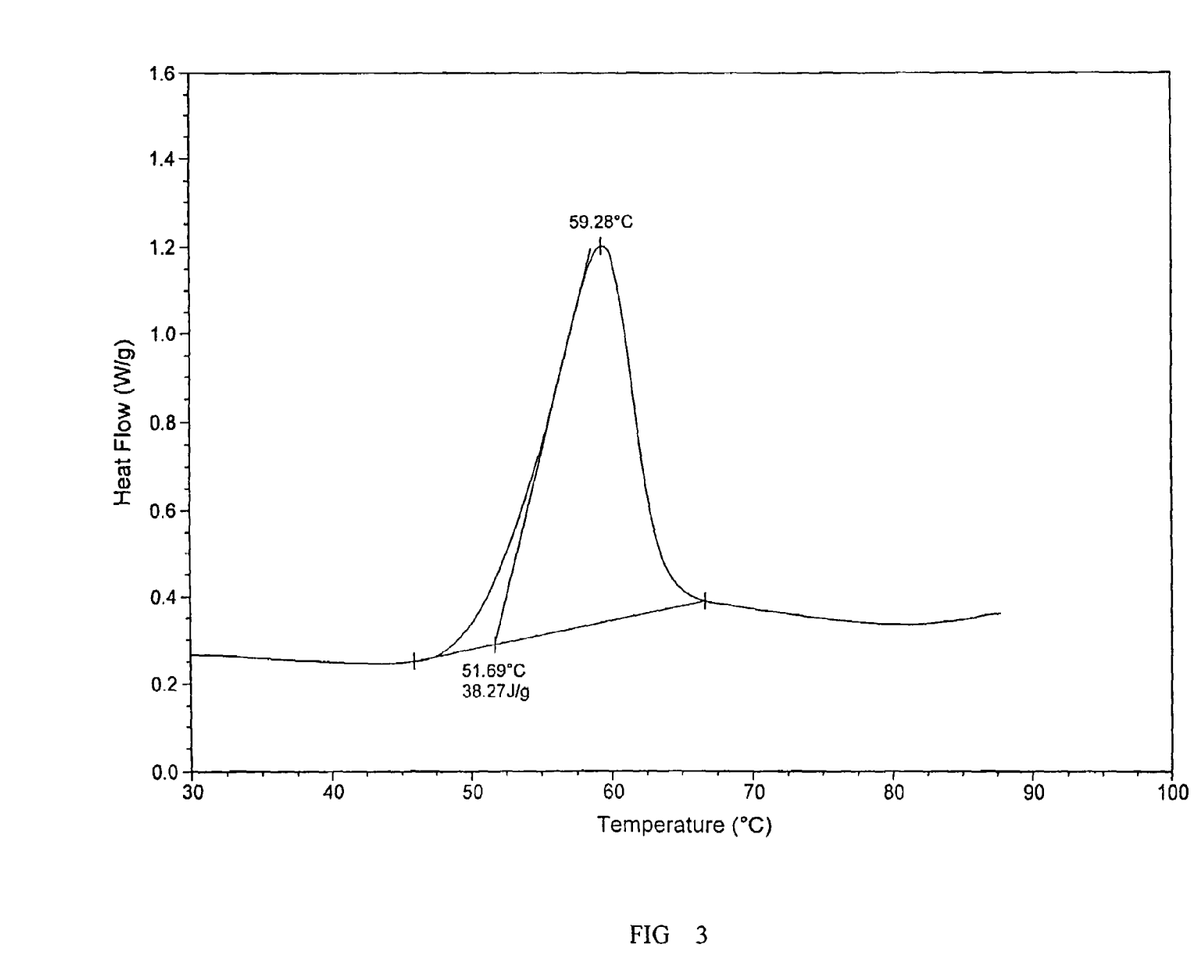
FIG. 3: The DSC profile of citalopram diol intermediate base crystal prepared as described in Example 1, where ethanol was used as solvent.

B. To 100 g citalopram diol intermediate free base oil substance, 300 mL ethanol was added and the mixture was heated until the oil substance was dissolved entirely. Then 140 ml water was added and the solution was stirred. After the solution cooled down, crystal seed was added and the solution was placed aside at 5° C. After about 24 hours, a large amount of crystal was crystallized. The solution was filtrated and 94.0 g high pure racemic citalopram diol intermediate base crystal was obtained. Its melting point was measured with thermometer, which is 48-52° C. Its extrapolate starting temperature of the DSC measured melting point (DSC, Onset) is 51.69° C., the peak value (DSC, Onset) is 59.28° C., (refer to FIG. 3), the enthalpy is 38.27 J/g. For the XRD Spectra, refer to FIG. 4. The purity of the product was 99.9% (HPLC, area normalization method), and the yield was 94.0%.

C. To 120 g citalopram diol intermediate hydrochloric salt, namely 4-dimethylamino-1-(4-bromo-2-hydroxylmethylphenyl)-1-(4-fluorophenyl)-butyl-1-ol, which had a purity of 94.6% and contained 3.0% (w/w) impurities of the previous mentioned Formula III (wherein Z is Br), 400 ml hot water and 40 ml ethanol were added. After the salt was dissolved entirely, 12 g active carbon was added and the solution was stirred for 30 min. Then the solution was filtrated and the active carbon filtrated cake was washed with 20 ml hot water. The washing liquid was merged into the filtrate and the filtrate was concentrated to a residue volume of 240 ml under vacuum in a hot water bath. Then the solution was placed at 5° C. for about 24 hours and a large amount of crystal was crystallized. The solution was filtrated to obtain citalopram diol intermediate hydrochloric salt crystal. The obtained crystal salt contained 2.9% (w/w) impurities of the previous mentioned Formula III (wherein Z is Br). 100 g obtained crystal salt was suspended and mixed in 400 ml isopropyl ether and the pH of the suspension was adjusted to above 9 with NaOH solution. The lower water phase was separated and discarded. The organic phase was dried, concentrated under vacuum to eliminate part of isopropyl ether. Then to the 160 ml residue that still contained isopropyl ether, 400 ml n-heptane was added and stirred to obtain crystal. The obtained crystal was recrystallized in 70% ethanol solution and citalopram diol intermediate free base crystal with a purity of 99.9% and a yield of 91.2% was obtained.

Example 2

Resolution of S-Citalopram Diol Intermediate

A. To 40 g citalopram diol intermediate free base crystal prepared in Example 1 (purity: 99.9%, HPLC, area normalization method), 360 ml isopropanol was added and the solution was heated until the crystal was dissolved entirely. 23.6 g D-di-4-methylbenzyol tartaric acid was added and dissolved, the solution was placed at room temperature for 12 hours. The crystal crystallized and was filtrated, washed with small amount of isopropanol to obtain S-citalopram diol intermediate—-D-di-4-methylbenzyol tartaric acid salt crystal. The obtained salt was then suspended and mixed in toluene, added with NaOH solution and stirred. The solution was placed aside, the organic and inorganic layer was separated. The toluene layer was heated, concentrated under vacuum to obtain 14 g S-citalopram diol intermediate oil substance (yield: 70%, purity: 99.9%), in which there was 0.5% R-citalopram diol intermediate (chiral HPLC).

B. To 40 g citalopram diol intermediate free base crystal prepared in Example 1 (purity: 99.9%, HPLC, area normalization method), 360 ml isopropanol was added and the solution was heated until the crystal was dissolved entirely. 23.6 g L-di-4-methylbenzyol tartaric acid was added and dissolved, the solution was placed at room temperature for 12 hours. The crystal crystallized (the mother liquor would be used in C) and was filtrated, washed with small amount of isopropanol to obtain R-citalopram diol intermediate—L-di-4-methylbenzyol tartaric acid salt crystal. The obtained salt was then suspended and mixed in toluene, added with NaOH solution and stirred. The solution was placed aside, the organic and inorganic layer was separated. The toluene layer was heated, concentrated under reduced pressure to obtain 14 g R-citalopram diol intermediate oil substance (yield: 70%, purity: 99.9%), in which there was 0.4% S-citalopram diol intermediate (chiral HPLC).

C. The mother liquor B of Example 2 was concentrated under reduced pressure, 100 mL isopropyl ether and NaOH was added. The mixture was stirred vigorously and its PH was adjusted to above 10. Then the lower water layer was discarded and the organic layer was dried, concentrated under reduced pressure to eliminate part of isopropyl ether to obtain the solution of non-racemic S-citalopram diol intermediate mixture that contained lesser R-citalopram diol intermediate, wherein S-enantiomer constituted 76.9%, R-enantiomer constituted 23.1% (chiral HPLC). To the residue solution that still contained some isopropyl ether, 80 mL n-heptane was added and stirred, then citalopram diol intermediate was added as crystal seed and crystallization was carried out at 5° C. After 48 hours, the solution was filtrated and the precipitated crystal was separated from the mother liquor. The mother liquor was evaporated to obtain the oil substance of S-enantiomer base, in which S-enantiomer constituted 99.1%, R-enantiomer constituted 0.9% (chiral HPLC). While in the precipitated crystal, S-enantiomer constituted 50.1%, R-enantiomer constituted 49.9% (chiral HPLC).

D. To 50 g non-racemic mixture of R-citalopram diol intermediate and S-citalopram diol intermediate, in which R-enantiomer constituted 76.9%, S-enantiomer constituted 23.1%, 120 mL 10% ethanol solution was added and the solution was heated, then crystallization was carried out at −5° C. After 48 hours, the solution was filtrated and the precipitated crystal was separated from the mother liquor. The mother liquor was evaporated to obtain the oil substance, in which R-enantiomer constituted 98.8%, S-enantiomer constituted 1.2% (chiral HPLC). While in the precipitated crystal, R-enantiomer constituted 51.3%, S-enantiomer constituted 48.7% (chiral HPLC).

Example 3

Preparation of Citalopram

To 20 g citalopram diol intermediate base crystal obtained in Example 1, 200 ml toluene and 80 g phosphoric acid were added, the solution was stirred at 80° C. for 2.5 hours and then cooled down to 50° C. with ice bath, its PH was adjusted to 10 with 20% NaOH solution. Then toluene solution was separated, washed with water and dried, disposed with silica gel and filtrated, evaporated to eliminate toluene to obtain 17.5 g citalopram oil substance. The purity of the product was 99.65% (HPLC, area normalization method), and the yield was over 86%.

Example 4

Preparation of Citalopram Hydrobromic Salt 10 g citalopram obtained in Example 3 was heated and dissolved in 40 mL isopropanol. After cooled down, pH of the solution was adjusted to 6-7 with bromic acid. The mixture was disposed with active carbon and filtrated, cooled down and placed aside to crystallize. Then the solution was filtrated and washed to obtain citalopram hydrobromic salt crystal. The obtained salt crystal was recrystallized to obtain 9.82 g citalopram hydrobromic salt crystal with the yield of 88.2% and the purity of 99.9% (HPLC, area normalization method).

Example 5

Preparation of S-Citalopram and its Oxalate Salt 20 g S-citalopram diol intermediate base obtained in Example 2 was dissolved in 430 ml toluene and 23 ml triethylamine was added. The solution was placed in ice bath and stirred, 5.14 ml methyl sulfochloride (dissolved in 30 ml toluene) was added dropwise. After the reaction was finished, the mixture was washed twice with 0.1M NaOH solution, the organic phase was dried with anhydrous $K_2CO_3$ and filtrated. The filtrate was concentrated to obtain 15.8 g S-citalopram oil substance. The obtained S-citalopram oil substance was dissolved in 80 ml acetone and heated, 6.15 g oxalic acid was added and dissolved, then the reaction mixture was disposed with active carbon, filtrated, cooled and crystallized. The crystal was filtrated and washed with small amount of acetone to obtain S-citalopram oxalate salt crystal, and the obtained oxalate salt crystal was recrystallized one or more times with acetone. The product, with a yield of 81.8% and a purity of 99.9% (w/w) (HPLC), contained 0.5% R-citalopram oxalate salt (chiral HPLC).

What is claimed is:

1. A crystalline base of Formula I comprising a crystal of a mixture of both S- and R-enantiomer of Formula I wherein the ratio of S- and R-enantiomer is between 0.5 and 1.5, wherein its extrapolate starting temperature of the Differential Scanning Calorimetry (DSC) measured melting point is 98.63° C., the peak value is 104.18° C.

2. A crystalline base of Formula I comprising a crystal of a mixture of both S- and R-enantiomer of Formula I wherein the ratio of S- and R-enantiomer is between 0.5 and 1.5, wherein its extrapolate starting temperature of the Differential Scanning Calorimetry (DSC) measured melting point is 51.69° C., the peak value is 59.28° C.

3. A method for preparing the crystalline base of claim 1, comprising the steps of:
    dissolving a citalopram diol intermediate free base oil substance in a single- or multi-component solvent,
    crystallizing the citalopram diol intermediate free base oil substance one or more times, and
    separating and obtaining a citalopram diol intermediate free base crystal.

4. The method of claim 3 wherein the solvent is
    a single component or a multi-component solvent that can dissolve citalopram diol intermediate free base, or
    a mixture of the single component solvent and the multi-component solvent, or
    a bi-component or multi-component mixture of water and one or more water soluble solvents that can dissolve citalopram diol intermediate free base.

5. The method of claim 3 wherein the solvent is a $C_{1-4}$ alcohol, a bi-component or multi-component mixture of a $C_{1-4}$ alcohol and water, an ester with more than four carbon atoms, a $C_{3-8}$ hydrocarbon and/or cycloparaffin, or a mixture of an ester with more than three carbon atoms and/or cycloparaffin.

6. The method of claim 5 wherein the solvent is a 60%~90% methanol solution, a 60%~90% ethanol solution, an isopropyl ether, or a mixture of isopropyl ether and hexane.

7. The method of claim 6 wherein the solvent is a 70% ethanol solution, a mixture of isopropyl ether and hexane (v/v=1:2), or a mixture of isopropyl ether and heptane (v/v=1:2).

8. The method of claim 3 wherein the crystallization temperature is between −40° C. and the boiling point of the solvent.

9. The method of claim 8 wherein the crystallization temperature is between −20° C. and 60° C.

10. The method of claim 9 wherein the crystallization temperature is between −5° C. and room temperature.

11. A method for preparing the crystalline base of claim 1, comprising the step of directly crystallizing a citalopram diol intermediate free base oil substance to obtain a citalopram diol intermediate free base crystal.

12. The crystalline base of claim 1, wherein the ratio of S- and R-enantiomer is between 0.8 and 1.2.

13. The crystalline base of claim 1, wherein the ratio of S- and R-enantiomer is 1.0 and the crystalline base is a racemic crystalline base.

14. The crystalline base of claim 2, wherein the ratio of S- and R-enantiomer is between 0.8 and 1.2.

15. The crystalline base of claim 3, wherein the ratio of S- and R-enantiomer is 1.0 and the crystalline base is a racemic crystalline base.

16. A method for preparing the crystalline base of claim 2, comprising the steps of:
    dissolving a citalopram diol intermediate free base oil substance in a single- or multi-component solvent,
    crystallizing the citalopram diol intermediate free base oil substance one or more times, and
    separating and obtaining a citalopram diol intermediate free base crystal.

17. The method of claim 16 wherein the solvent is
    a single component or a multi-component solvent that can dissolve citalopram diol intermediate free base, or
    a mixture of the single component solvent and the multi-component solvent, or
    a bi-component or multi-component mixture of water and one or more water soluble solvents that can dissolve citalopram diol intermediate free base.

18. The method of claim 16 wherein the solvent is a $C_{1-4}$ alcohol, a bi-component or multi-component mixture of a $C_{1-4}$ alcohol and water, an ester with more than four carbon atoms, a $C_{3-8}$ hydrocarbon and/or cycloparaffin, or a mixture of an ester with more than three carbon atoms and/or cycloparaffin.

19. The method of claim 18 wherein the solvent is a 60%~90% methanol solution, a 60%~90% ethanol solution, an isopropyl ether, or a mixture of isopropyl ether and hexane.

20. The method of claim 19 wherein the solvent is a 70% ethanol solution, a mixture of isopropyl ether and hexane (v/v=1:2), or a mixture of isopropyl ether and heptane (v/v=1:2).

21. The method of claim 16 wherein the crystallization temperature is between −40° C. and the boiling point of the solvent.

22. The method of claim 21 wherein the crystallization temperature is between −20° C. and 60° C.

23. The method of claim 22 wherein the crystallization temperature is between −5° C. and room temperature.

24. A method for preparing the crystalline base of claim 2, comprising the step of directly crystallizing a citalopram diol intermediate free base oil substance to obtain a citalopram diol intermediate free base crystal.

* * * * *